United States Patent
Tsujita

(10) Patent No.: US 8,515,142 B2
(45) Date of Patent: *Aug. 20, 2013

(54) IMAGE PROCESSING APPARATUS, IMAGE PROCESSING METHOD, AND IMAGE PROCESSING PROGRAM

(75) Inventor: Kazuhiro Tsujita, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 965 days.

This patent is subject to a terminal disclaimer.

(21) Appl. No.: 12/547,307

(22) Filed: Aug. 25, 2009

(65) Prior Publication Data

US 2010/0054576 A1  Mar. 4, 2010

(30) Foreign Application Priority Data

Aug. 26, 2008 (JP) ................. 2008-216483

(51) Int. Cl.
*G06K 9/00* (2006.01)
(52) U.S. Cl.
USPC .......................................... 382/128; 128/922
(58) Field of Classification Search
USPC .............. 382/128–131; 128/922; 702/19–21
See application file for complete search history.

(56) References Cited

U.S. PATENT DOCUMENTS

| | | | |
|---|---|---|---|
| 5,813,987 A * | 9/1998 | Modell et al. | 600/473 |
| 5,879,284 A | 3/1999 | Tsujita | |
| 6,230,046 B1 * | 5/2001 | Crane et al. | 600/476 |
| 6,563,906 B2 * | 5/2003 | Hussein et al. | 378/89 |
| 7,336,990 B2 * | 2/2008 | Genet et al. | 600/477 |
| 7,573,499 B2 * | 8/2009 | Doguchi et al. | 348/65 |
| 7,647,085 B2 * | 1/2010 | Cane et al. | 600/410 |
| 7,944,466 B2 * | 5/2011 | Abe et al. | 348/71 |
| 8,180,435 B2 * | 5/2012 | Rice et al. | 600/473 |
| 8,358,821 B2 * | 1/2013 | Yamaguchi et al. | 382/128 |
| 2003/0002028 A1 * | 1/2003 | Rice et al. | 356/39 |
| 2004/0015062 A1 * | 1/2004 | Ntziachristos et al. | 600/312 |
| 2005/0059868 A1 * | 3/2005 | Schurman | 600/323 |

(Continued)

FOREIGN PATENT DOCUMENTS

| JP | 08322821 | * 12/1996 |
|---|---|---|
| JP | 2003-93336 A | 4/2003 |

OTHER PUBLICATIONS

Wieringa et al. "Remote Non-invasive Stereoscopic Imaging of Blood Bessels: First In-vivo Results of a New Multispectral Contrast Enhancement Technology." Annals of Biomedical Engineering, vol. 34, No. 12, Dec. 2006 pp. 1870-1878.*

*Primary Examiner* — Tran Nguyen
*Assistant Examiner* — Anita Coupe
(74) *Attorney, Agent, or Firm* — Birch, Stewart, Kolasch & Birch, LLP

(57) ABSTRACT

The image quality of fluorescent images of blood vessels obtained by imaging blood vessels emitting fluorescence is improved. Living tissue within a body cavity is imaged by an endoscope while fluorescent pigments within blood vessels are emitting fluorescence due to irradiation of excitation light. At this time, a standard observation image obtained by imaging the same portion of the body cavity while white light is being irradiated, and a fluorescent image obtained by imaging while the excitation light is being irradiated are obtained. A plurality of spectral images having different wavelength ranges are generated. The depth position of blood vessels within a region of interest are judged by a depth position judging unit. Thereafter, an image processing unit administers an image process using image processing conditions corresponding to the depth position of the blood vessels, and a processed image is displayed by a display device.

10 Claims, 5 Drawing Sheets

(56) References Cited

U.S. PATENT DOCUMENTS

| | | | |
|---|---|---|---|
| 2008/0253513 A1* | 10/2008 | Boyden et al. | 378/38 |
| 2008/0253524 A1* | 10/2008 | Boyden et al. | 378/87 |
| 2009/0147096 A1* | 6/2009 | Yamaguchi et al. | 348/222.1 |
| 2009/0147998 A1* | 6/2009 | Yamaguchi et al. | 382/106 |
| 2009/0147999 A1* | 6/2009 | Maeda et al. | 382/106 |
| 2010/0067766 A1* | 3/2010 | Vija | 382/131 |

* cited by examiner

DB

| PARAMETER (WAVELENGTH) | $M_{j0}$ | $M_{j1}$ | $M_{j2}$ |
|---|---|---|---|
| p1 | 0.000083 | −0.00188 | 0.003592 |
| ⋮ | ⋮ | ⋮ | ⋮ |
| p18 | −0.00115 | 0.000569 | 0.003325 |
| p19 | −0.00118 | 0.001149 | 0.002771 |
| p20 | −0.00118 | 0.001731 | 0.0022 |
| p21 | −0.00119 | 0.002346 | 0.0016 |
| p22 | −0.00119 | 0.00298 | 0.000983 |
| p23 | −0.00119 | 0.003633 | 0.000352 |
| ⋮ | ⋮ | ⋮ | ⋮ |
| p43 | 0.003236 | 0.001377 | −0.00159 |
| p44 | 0.003656 | 0.000671 | −0.00126 |
| p45 | 0.004022 | 0.000068 | −0.00097 |
| p46 | 0.004342 | −0.00046 | −0.00073 |
| p47 | 0.00459 | −0.00088 | −0.00051 |
| p48 | 0.004779 | −0.00121 | −0.00034 |
| p49 | 0.004922 | −0.00148 | −0.00018 |
| p50 | 0.005048 | −0.00172 | −0.000036 |
| p51 | 0.005152 | −0.00192 | 0.000088 |
| p52 | 0.005215 | −0.00207 | 0.000217 |
| ⋮ | ⋮ | ⋮ | ⋮ |
| p61 | 0.00548 | −0.00229 | 0.00453 |

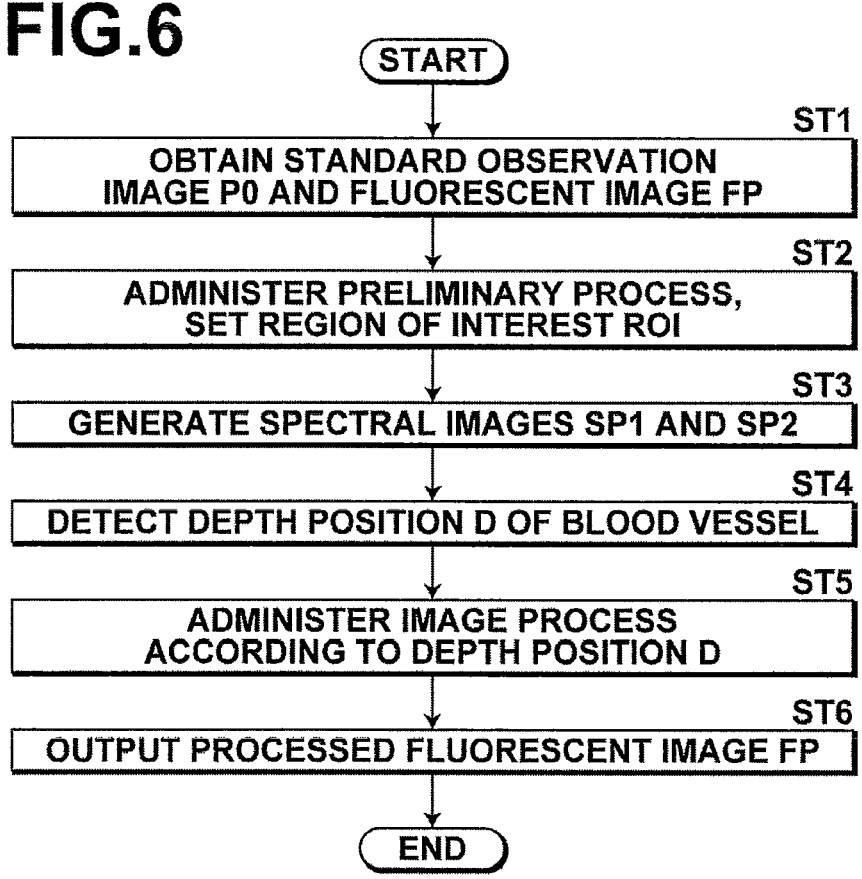

IMAGE PROCESSING APPARATUS, IMAGE PROCESSING METHOD, AND IMAGE PROCESSING PROGRAM

BACKGROUND OF THE INVENTION

1. Field of the Invention

The present invention is related to an image processing apparatus, an image processing method, and an image processing program for administering image processes onto fluorescent images that represent blood vessels, obtained by an endoscope.

2. Description of the Related Art

Recently, NBI (Narrow Band Imaging) apparatuses which have built in combinations of narrow bandpass filters and which are employed to perform spectral imaging based on spectral reflectance of digestive organs (gastric mucosa and the like), are gaining attention as imaging apparatuses such as electronic endoscopes that employ solid state imaging elements. These apparatuses are equipped with narrow (wavelength) bandpass filters instead of rotating frame sequential R (red), G (green), and B (blue) filters. Illuminating light beams are sequentially output via these narrow bandpass filters, and spectral images are formed by administering processes similar to those administered onto RGB signals while changing the weighting of three signals obtained by each illuminating light beam. Fine structures, which had heretofore been unobtainable, are capable of being extracted within digestive organs such as stomachs and large intestines from these spectral images.

On the other hand, Japanese Unexamined Patent Publication No. 2003-093336 discloses forming spectral images by administering calculation processes on image signals obtained by imaging using white light using a simultaneous method in which a fine mosaic color filter is provided on a solid state imaging element, instead of the aforementioned frame sequential method that employs the narrow bandpass filters. In this method, relationships among numerical data that represent color sensitivity properties of R, G, and B, and numerical data that represent spectral properties of specific narrow wavelength bands are obtained as matrix data (set of coefficients). Spectral image signals, which are estimations of spectral images obtained via narrow bandpass filters, are obtained by calculations among the matrix data and R, G, and B signals. In the case that the spectral images are obtained by calculations in this manner, it is not necessary to prepare a plurality of filters that correspond to each desired wavelength range. In addition, replacement of filters is obviated. Therefore, the size of an apparatus that employs this method can be kept small, and costs can be suppressed.

Meanwhile, a method in which blood vessels, cancer cells and the like are labeled with fluorescent reagents and fluorescent images thereof are observed is employed in the field of living tissue observation. Applying the aforementioned techniques regarding spectral images to obtain the fluorescent images is being considered. Fluorescent images are employed to understand the accurate positions of blood vessels by intravenously injecting a fluorescent reagent, such as ICG (Indo Cyanine Green). Here, by obtaining light in the near infrared region of 700 nm to 1300 nm, at which attenuation due to living tissue is small, as the fluorescent images, the positions of blood vessels can be specified even at depths of approximately 2 mm from a surface layer.

In addition, an image processing method is disclosed, in which blur within images is estimated based on prognostic simulations and point spreads of actually obtained images, then a reconstructing process is administered, to obtain sharper images of blood vessels (refer to U.S. Pat. No. 5,879,284, for example).

Here, applying the blood vessel emphasizing process disclosed in U.S. Pat. No. 5,879,284 to fluorescent images maybe considered, in order to improve the sharpness of blood vessel images within fluorescent images. However, the degree of blur of blood vessel images differs within fluorescent images according to the depth positions of the blood vessels. Therefore, there is a problem that image quality does not improve in cases that image quality improving processes are administered employing a uniform point spread. Meanwhile, the depth positions of blood vessels cannot be discriminated within fluorescent images, and as a result, there is a problem that it is difficult to improve the image quality of fluorescent images.

SUMMARY OF THE INVENTION

The present invention has been developed in view of the foregoing circumstances. It is an object of the present invention to provide an image processing apparatus, an image processing method, and an image processing program which are capable of administering image processes that improve the image quality of fluorescent images appropriately, according to the depth positions of blood vessels.

An image processing apparatus of the present invention comprises:

fluorescent image obtaining means for obtaining a fluorescent image by imaging fluorescence emitted by substances within blood vessels when an excitation light beam is irradiated onto the blood vessels;

spectral image obtaining means for obtaining a plurality of spectral images, each of a different wavelength range, of the same blood vessels of which the fluorescent image is obtained;

depth position judging means for judging the depth position at which the blood vessels exist, employing the plurality of spectral images obtained by the spectral image obtaining means; and image processing means for changing image processing conditions according to the depth position of the blood vessels judged by the depth position judging means, and administering a blood vessel emphasizing process on the fluorescent image.

An image processing method of the present invention comprises the steps of:

obtaining a fluorescent image by imaging fluorescence emitted by substances within blood vessels when an excitation light beam is irradiated onto the blood vessels;

obtaining a plurality of spectral images, each of a different wavelength range, of the same blood vessels of which the fluorescent image is obtained;

judging the depth position at which the blood vessels exist, employing the plurality of obtained spectral images;

changing image processing conditions according to the depth position of the blood vessels judged by the depth position judging means; and administering a blood vessel emphasizing image process on the fluorescent image.

An image processing program of the present invention causes a computer to execute the procedures of:

obtaining a fluorescent image by imaging fluorescence emitted by substances within blood vessels when an excitation light beam is irradiated onto the blood vessels;

obtaining a plurality of spectral images, each of a different wavelength range, of the same blood vessels of which the fluorescent image is obtained;

judging the depth position at which the blood vessels exist, employing the plurality of obtained spectral images;

changing image processing conditions according to the depth position of the blood vessels judged by the depth position judging means; and administering a blood vessel emphasizing image process on the fluorescent image.

Here, the plurality of spectral images may be obtained in any manner, as long as they are spectral images of different wavelength ranges. For example, the plurality of spectral images may be estimated spectral images, which are generated by administering matrix calculations onto a standard observation image obtained by imaging the blood vessels irradiated with white light. Alternatively, the plurality of spectral images may be obtained by irradiating two narrow bandwidth light beams having different wavelength ranges onto the blood vessels, and imaging the blood vessels to obtain spectral images corresponding to each narrow wavelength band.

Note that the type of emphasizing process administered by the image processing means maybe of any type, as long as the blood vessel emphasizing process is administered after changing the image processing conditions according to the depth position of the blood vessels. For example, the image processing conditions which are changed by the image processing means may be a plurality of point spread functions corresponding to the depth positions of the blood vessels; and the image processing means may select a point spread function to be employed to process the fluorescent image corresponding to the judgment results obtained by the depth position judging means.

Alternatively, the image processing means may extract the outlines of the blood vessels, based on the widths of fluorescence and blur spread within the fluorescent image, and administers the blood vessel emphasizing process by overlapping the extracted outlines of the blood vessels onto the fluorescent image. In this case, the widths of blur spread, which differ according to the depth position of the blood vessels, are the image processing conditions.

The depth position judging means may be of any configuration, as long as it judges the depth positions at which blood vessels are present employing the plurality of spectral images. The depth position judging means may judge the depth position of the blood vessels based on the penetration depth of the wavelengths of the spectral images, by judging whether blood vessel images can be extracted from each of the spectral images.

As a specific example of such a configuration, the spectral images may include a first spectral image obtained by light having a wavelength of approximately 430 nm, and a second spectral image obtained by light having a wavelength of approximately 570 nm; and the depth position judging means may comprise: blood vessel image extracting means for extracting the blood vessel images from each of the first spectral image and the second spectral image; blood vessel presence judging means for judging whether the blood vessel images are present in each of the spectral images, based on the extraction results obtained by the blood vessel image extracting means; and depth position detecting means, for judging that the blood vessels are at a first depth position close to the surface in the case that the blood vessel presence judging means judges that the blood vessel images are present within the first spectral image, judging that the blood vessels are at a second depth position deeper than the first depth position in the case that the blood vessel presence judging means judges that the blood vessel images are present within the second spectral image, and judging that the blood vessels are at a third depth position deeper than the second depth position in the case that the blood vessel presence judging means judges that the blood vessel images are present in neither the first spectral image nor the second spectral image.

The judgment of the depth position of blood vessels by the depth position judging means and the image process administered by the image processing means may be performed with respect to the entirety of the spectral images and the fluorescent image. Alternatively, the image processing apparatus may further comprise: region of interest setting means for setting a region of interest within the fluorescent image, and the judgment of the depth position of the blood vessels by the depth position judging means and the image process administered by the image processing means may be performed within the region of interest set by the region of interest setting means.

The image processing method of the present invention may be provided as a program that causes a computer to execute the method. The program may be provided being recorded on a computer readable medium. Those who are skilled in the art would know that computer readable media are not limited to any specific type of device, and include, but are not limited to: floppy disks, CD's, RAM's, ROM's, hard disks, magnetic tapes, and internet downloads, in which computer instructions can be store and/or transmitted. Transmission of the computer instructions through a network or through wireless transmission means is also within the scope of this invention. Additionally, computer instructions include, but are not limited to: source, object, and executable code, and can be in any language, including higher level languages, assembly language, and machine language.

According to the image processing apparatus, the image processing method, and the image processing program of the present invention, a fluorescent image is obtained by imaging fluorescence emitted by substances within blood vessels when an excitation light beam is irradiated onto the blood vessels; a plurality of spectral images, each of a different wavelength range, are obtained of the same blood vessels of which the fluorescent image is obtained; the depth position at which the blood vessels exist is judged, employing the plurality of obtained spectral images; image processing conditions are changed according to the depth position of the blood vessels judged by the depth position judging means; and the blood vessel emphasizing process is administered on the fluorescent image. That is, the depth position of the blood vessels is ascertained from the spectral images, by utilizing the fact that penetration depths of light into living tissue differ according to the wavelength of light. Then, image processing conditions suited to the depth position of the blood vessels are employed to administer the blood vessel emphasizing process onto the fluorescent image, in which blood vessel images appear differently according to the depth positions thereof. Therefore, the sharpness and resolution of the blood vessel images can be improved.

A configuration may be adopted, in which the image processing conditions which are changed by the image processing means are a plurality of point spread functions corresponding to the depth positions of the blood vessels; and the image processing means selects a point spread function to be employed to process the fluorescent image corresponding to the judgment results obtained by the depth position judging means. In this case, even if the degree of blur of the blood vessel image differs within the fluorescent image due to scattering of fluorescence or the like, image processing conditions suited for the depth position of the blood vessels can be employed to administer the blood vessel emphasizing process. Therefore, the sharpness and resolution of the blood vessel images can be improved.

Alternatively, the image processing means may extract the outlines of the blood vessels, based on the widths of fluorescence and blur spread within the fluorescent image, and may administer the blood vessel emphasizing process by overlapping the extracted outlines of the blood vessels onto the fluorescent image, and the widths of blur spread, which differ according to the depth position of the blood vessels, may be the image processing conditions. In this case, even if the degree of blur of the blood vessel image differs within the fluorescent image due to scattering of fluorescence or the like, the width of blur spread can be set according to the depth position of the blood vessels. Therefore, the sharpness and resolution of the blood vessel images can be improved.

A configuration may be adopted, in which the plurality of spectral images maybe estimated spectral images, which are generated by administering matrix calculations onto a standard observation image obtained by imaging the blood vessels irradiated with white light. In this case, spectral images of different wavelengths, each having different penetration depths, can be obtained efficiently.

A configuration may be adopted, wherein the depth position judging means judges the depth position of the blood vessels based on the penetration depth of the wavelengths of the spectral images, by judging whether blood vessel images can be extracted from each of the spectral images. In this case, the depth position of blood vessels can be accurately judged from the spectral images, by utilizing the fact that penetration depths of light into living tissue differ according to the wavelength of light.

As a specific example of such a configuration, the spectral images may include a first spectral image obtained by light having a wavelength of approximately 430 nm, and a second spectral image obtained by light having a wavelength of approximately 570 nm; and the depth position judging means may comprise: blood vessel image extracting means for extracting the blood vessel images from each of the first spectral image and the second spectral image; blood vessel presence judging means for judging whether the blood vessel images are present in each of the spectral images, based on the extraction results obtained by the blood vessel image extracting means; and depth position detecting means, for judging that the blood vessels are at a first depth position close to the surface in the case that the blood vessel presence judging means judges that the blood vessel images are present within the first spectral image, judging that the blood vessels are at a second depth position deeper than the first depth position in the case that the blood vessel presence judging means judges that the blood vessel images are present within the second spectral image, and judging that the blood vessels are at a third depth position deeper than the second depth position in the case that the blood vessel presence judging means judges that the blood vessel images are present in neither the first spectral image nor the second spectral image. In this case, the depth position of the blood vessels can be judged accurately.

The image processing apparatus may further comprise: region of interest setting means for setting a region of interest within the fluorescent image, and the judgment of the depth position of the blood vessels by the depth position judging means and the image process administered by the image processing means may be performed within the region of interest set by the region of interest setting means. In this case, the time required for image processing may be shortened, and processing can be performed efficiently.

BRIEF DESCRIPTION OF THE DRAWINGS

FIG. 6 is a flow chart that illustrates a preferred embodiment of the image processing method of the present invention.

DESCRIPTION OF THE PREFERRED EMBODIMENTS

Figure 1:
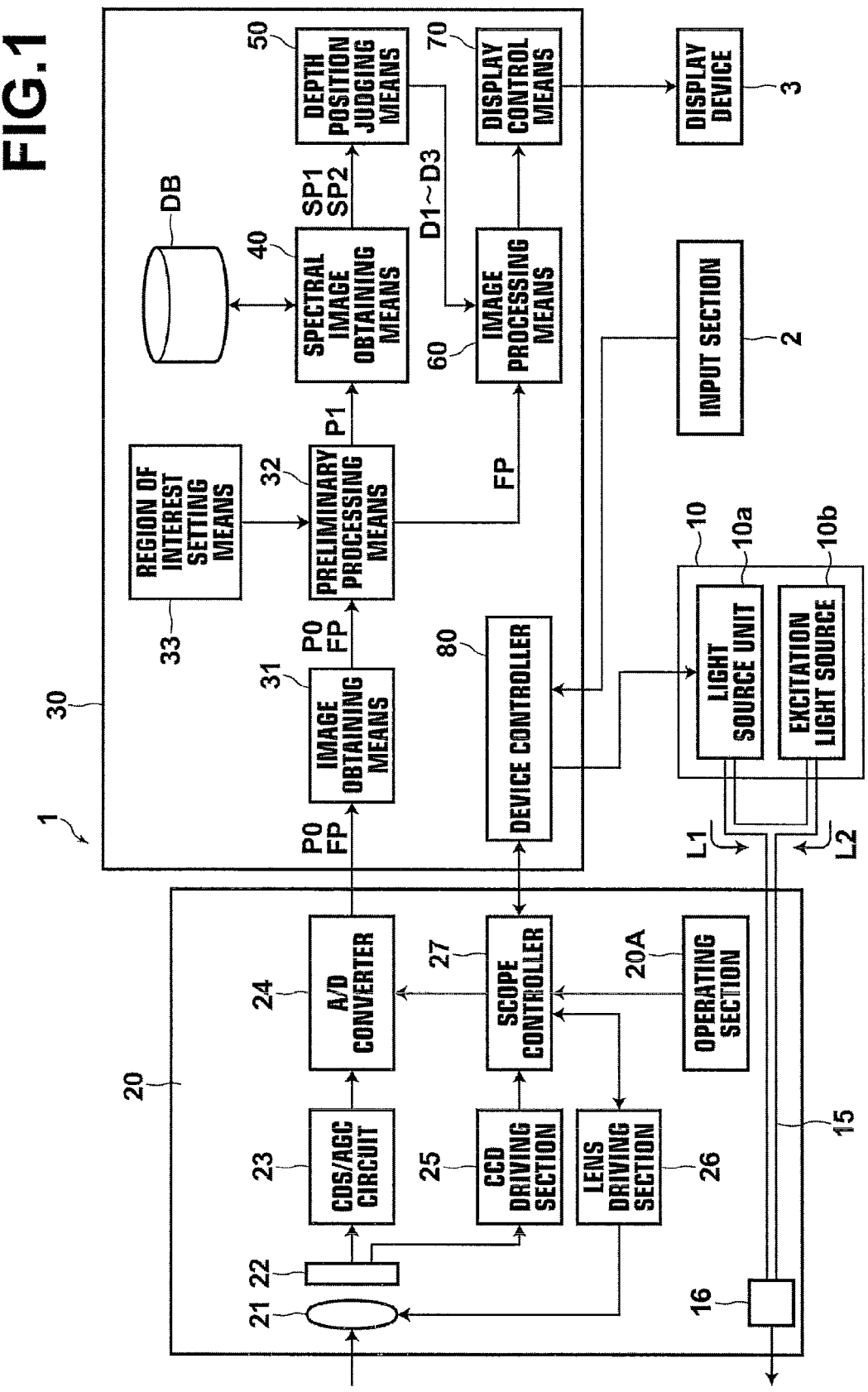
FIG. 1 is a block diagram that illustrates an endoscope that employs an image processing apparatus of the present invention.

Hereinafter, an embodiment of the present invention will be described with reference to the attached drawings. FIG. 1 is a block diagram that illustrates an endoscope 1 that employs the image processing apparatus of the present invention. The endoscope 1 is equipped with: a light source unit 10; a scope 20; and an image processing apparatus 30. Here, blood vessels, which are the targets of observation, are died with a fluorescent reagent having an excitation wavelength range of 600 nm to 1300 nm. Examples of such a reagent include: DyLight 680, which has an excitation wavelength of 682 nm and a fluorescence wavelength of 715 nm; Cy7, which has an excitation wavelength of 747 nm and a fluorescence wavelength of 776 nm; and ICG (Indo Cyanine Green), which has an excitation wavelength of 785 nm and a fluorescence wavelength of 805 nm.

The light source unit 10 irradiates light onto subjects to perform observation using the endoscope 1. The light source unit 10 is equipped with: a standard light source 10a, such as a xenon lamp, for performing standard observation; and an excitation light source 10b for performing fluorescent observation. The operations of the light source unit 10 are controlled by a device controller 80. The standard light source 10a emits white light, and the excitation light source 10b emits an excitation light beam having a wavelength of 682 nm or 747 nm, for example. The light source unit 10 is optically connected to a light guide 15 of the scope 20. The white light L1 and the excitation light beam L2 emitted by the light source unit 10 enters the light guide 15, and is irradiated onto subjects through an observation window 16.

The scope 20 includes: a focusing optical system 21; an imaging element 22; a CDS/AGC circuit 23; an A/D converter 24; a CCD driving section 25; a lens driving section 26; and the like. Each component of the scope 20 is controlled by a scope controller 27. The imaging element 22 is a CCD, a C-MOS or the like that obtains images by photoelectrically converting images of subjects which are focused thereon by the focusing optical system 21. The imaging element 22 may be a complementary color type having Mg (magenta), Ye (yellow), and Cy (cyan) color filters on the surface thereof, or a primary color type, having R (red), G (green), and B (blue) color filters on the surface thereof. Note that the operations of the imaging element 22 are controlled by the CCD driving section 25. When the imaging element 22 obtains image (video) signals, the CDS/AGC (Correlated Double Sampling/Automatic Gain Control) circuit 23 samples and amplifies the signals. The A/D converter converts the endoscope image output from the CDS/AGC circuit 17 into digital signals, and outputs the digital signals to the image processing apparatus 30.

The image processing apparatus 30 processes standard observation images and fluorescent images FP which are obtained by the scope 20, and is constituted by a DSP or the like. The image processing apparatus 30 is equipped with: an image obtaining means 31; a preliminary processing means 32; a region of interest setting means 33; a spectral image obtaining means 40; a depth position judging means 50; and an image processing means 60. The image obtaining means 31 obtains standard observation images P0, which are obtained by imaging blood vessels while the blood vessels are irradiated with the white light L1, and fluorescent images FP, which are obtained by imaging the blood vessels while the blood vessels are irradiated with the excitation light beam L2. Because the standard observation images P0 and the fluorescent images FP are obtained of the same portions of subjects, the standard observation images P0 and the fluorescent images FP are obtained by imaging using the time division method.

The preliminary processing means 32 administers preliminary processes onto the standard observation images P0 and the fluorescent images FP obtained by the image obtaining means 31. For example, in the case that the standard observation images P0 and the fluorescent images FP are of the YCC color system, the preliminary processing means 32 converts the images to an RGB color system. Further, the preliminary processing means 32 functions to perform gamma conversion, gradation adjustment, and the like.

The region of interest setting means 33 sets regions of interest ROI within the standard observation images P0 and the fluorescent images FP. For example, a rectangular region that includes a range at which the near infrared fluorescent intensity is greater than or equal to a predetermined value may be automatically set as a region of interest ROI. Note that the region of interest setting means 33 may be configured such that the regions of interest ROI are set according to input from an input section that includes a mouse, a keyboard, and the like to the device controller 80. It is preferable to set the regions of interest ROI such that they include only blood vessels and tissue/fat, such that spectral images SP1 and SP2 to be described later can be accurately obtained.

The spectral image obtaining means 40 generates estimated spectral images SP by performing matrix calculations on the standard observation images P0, employing matrix parameters. Note that the details of the operation of the spectral image obtaining means 40 are described in Japanese Unexamined Patent Publication No. 2003-093336. The spectral image obtaining means 40 generates the matrix calculation represented by the following Formula (1) to generate the estimated spectral images SP.

$$\begin{pmatrix} SP_r \\ SP_g \\ SP_b \end{pmatrix} = \begin{pmatrix} M_{00} & M_{01} & M_{02} \\ M_{10} & M_{11} & M_{12} \\ M_{20} & M_{20} & M_{22} \end{pmatrix} \cdot \begin{pmatrix} Pr \\ Pg \\ Pb \end{pmatrix} \quad (1)$$

Note that in Formula (1), SPr, SPg, and SPb are the R, G, and B components of the estimated spectral images SP, respectively, Pr, Pg, and Pb are the Rf G, and B components of the standard observation images P0, and the 3×3 matrix constituted by $M_{00}$ through $M_{22}$ are matrix parameters for performing the matrix calculation.

Note that eight sets of wavelengths, including: a standard set CH1 (λ1, λ2, λ3)=(400, 500, 600); blood vessel sets CH2 (λ1, λ2, λ3)=(470, 500, 670) and CH3 (λ1, λ2, λ3)=(475, 510, 685), for visualizing blood vessels; a tissue set CH5 (λ1, λ2, λ3)=(440, 480, 520) or (480, 510, 580) for visualizing specific tissues; a hemoglobin set CH6 (λ1, λ2, λ3)=(400, 430, 475) for visualizing differences between oxyhemoglobin and dioxyhemoglobin; a blood/carotene set CH7 (λ1, λ2, λ3)=(410, 450, 500); and a blood/cytoplasm set CH8 (λ1, λ2, λ3)=(420, 550, 600) are prepared.

Figure 2:
FIG. 2 is a table that illustrates examples of matrix parameters which are employed by a spectral image obtaining means of the image processing apparatus of FIG. 1, to perform matrix calculations.

FIG. 2 is a table that illustrates an example of a database DB. Parameters Pi ($M_{j0}$, $M_{j1}$, $M_{j2}$), wherein i is a symbol for differentiating parameter sets stored in the database DB and has values from 1 through 6, and j is the line number of the lines M within Formula (1) and has values from 0 through 2, are recorded in the database DB for each of 61 wavelength ranges from 400 nm through 700 nm, in 5 nm increments. An operator selects a wavelength set for estimated spectral images SP to be generated from among the wavelength sets CH2 through CH8, and inputs the selection via the input section 2. Then, the spectral image obtaining means 40 extracts matrix parameters ($M_{j0}$, $M_{j1}$, $M_{j2}$) corresponding to the wavelengths (λ1, λ2, λ3) of the selected wavelength set from the database DB, and sets the matrix parameters for Formula (1). For example, in the case that a wavelength set (λ1, λ2, λ3)=(500 nm, 620 nm, 650 nm) is selected as the wavelength set of spectral images to be generated, the spectral image obtaining means 40 assigns parameters $P_{21}$ corresponding to a central wavelength of 500 nm from among the 61 sets of parameters Pi to the line j=0 within the matrix M, to set ($M_{00}$, $M_{01}$, $M_{02}$) to (−0.00119, 0.002346, 0.0016). Similarly, parameters $P_{45}$ corresponding to a central wavelength of 620 nm are assigned to the line j=1 within the matrix M, to set ($M_{10}$, $M_{11}$, $M_{12}$) to (0.004022, 0.000068, −0.00097), and parameters $P_{51}$ corresponding to a central wavelength of 650 nm are assigned to the line j=2 within the matrix M, to set ($M_{20}$, $M_{21}$, $M_{22}$) to (0.005152, −0.00192, 0.000088). Then, the spectral image obtaining means performs the matrix calculation of Formula (1), employing the assigned parameters.

Further, the spectral image obtaining means 40 functions to automatically generate spectral images SP1 and SP2, which are employed to judge depth positions D of blood vessels, by performing matrix calculations with respect to the regions of interest ROI set by the region of interest setting means 33, in addition to generating the estimated spectral images SP selected by the operator. For example, the spectral image obtaining means 40 obtains a first spectral image SP1 having a wavelength λ1 of 430 nm, and a second spectral image SP2 having a wavelength λ2 of 570 nm.

Figure 3:
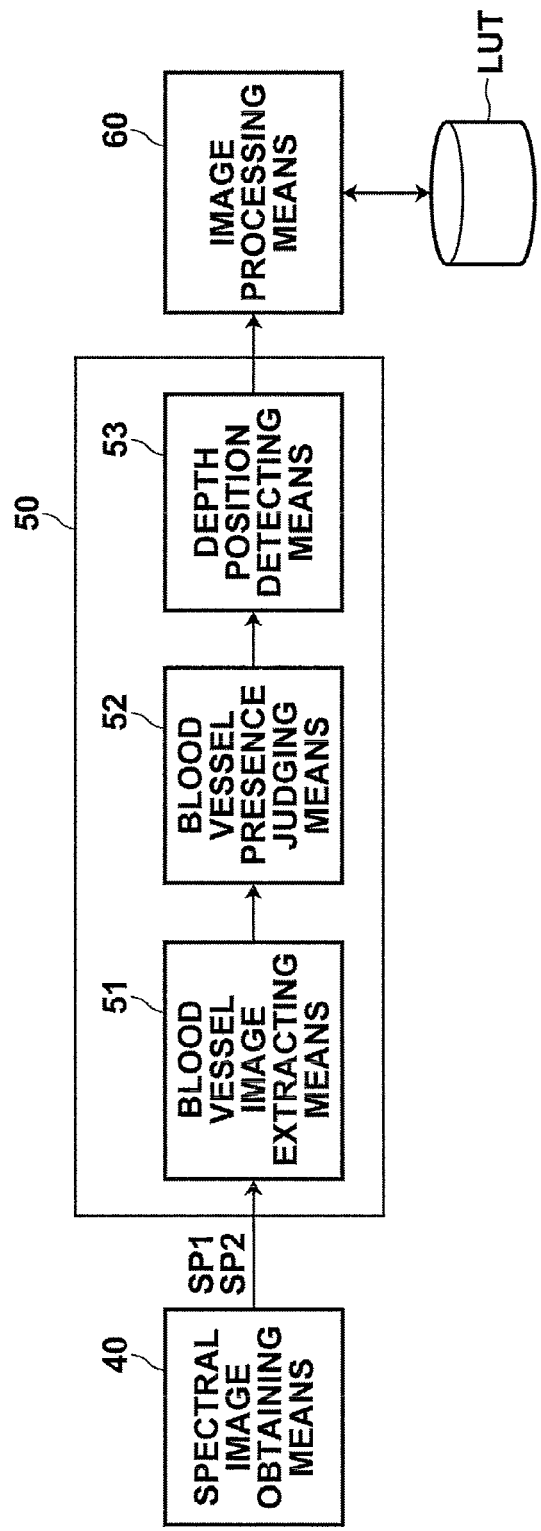
FIG. 3 is a block diagram that illustrates the spectral image obtaining means, a depth position judging means, and an image processing means of the image processing apparatus of FIG. 1.

The depth position judging means 50 judges the depth positions D at which blood vessels exist, employing the spectral images SP1 and SP2 obtained by the spectral image obtaining means 40. Here, the depth position judging means 50 judges the depth position D of the blood vessels based on the penetration depth of the wavelengths of the spectral images SP1 and SP2, by judging whether blood vessel images can be extracted from each of the spectral images SP1 and SP2. Specifically, the depth position judging means 50 is equipped with: a blood vessel image extracting means 51; a blood vessel presence judging means 52; and a depth position detecting means 53, as illustrated in FIG. 3.

The blood vessel image extracting means 51 administers a process to extract blood vessel images from the first spectral image SP1 and the second spectral image SP2. The blood vessel image extracting means 51 employs known blood vessel image extracting methods, such as that which utilizes an edge detection technique, to extract the blood vessels images.

The blood vessel presence judging means 52 judges whether the blood vessel images are present in the first spectral image SP1 and the second spectral image SP2, based on the extraction results obtained by the blood vessel image extracting means 51. The blood vessel presence judging means 52 may set a threshold value for pixel values, and the presence and lengths of linear patterns having pixel values greater than or equal to the threshold value are employed to judge whether the blood vessel images are present, for example. Further, the presence and lengths of linear patterns may be designated as features to be employed when extracting the blood vessel images by pattern matching or a neural network. Note that there may be cases in which blood vessel images are present in both the spectral image SP1 and the spectral image SP2. In these cases, the blood vessel presence judging means selects the spectral image that includes the blood vessel image having the larger area, to judge the spectral image in which the blood vessel image is most clearly pictured.

The depth position detecting means 53 judges the depth position D of blood vessels, based on the presence or absence of blood vessels in the spectral images SP1 and SP2, which is judged by the blood vessel presence judging means 52. Specifically, the depth position detecting means 53 judges that the blood vessels are at a first depth position D1 close to the surface (0 mm to 0.5 mm from the surface, for example) in the case that the blood vessel presence judging means 52 judges that the blood vessel images are present within the first spectral image SP1. Meanwhile, the depth position detecting means 53 judges that the blood vessels are at a second depth position D2 (0.5 mm to 1.5 mm from the surface, for example) deeper than the first depth position D1 in the case that the blood vessel presence judging means 52 judges that the blood vessel images are present within the second spectral image SP2. Further, the depth position detecting means 53 judges that the blood vessels are at a third depth position D3 (1.5 mm to 2.0 mm or more than 1.5 mm from the surface, for example) deeper than the second depth position D2 in the case that the blood vessel presence judging means judges that the blood vessel images are present in neither the first spectral image SP1 nor the second spectral image SP2.

The image processing means 60 administers image processes with respect to the fluorescent images FP under different image processing conditions RC, according to one of the depth positions D1 through D3 of the blood vessels which has been judged by the depth position judging means 50. Specifically, the image processing means 60 has a plurality of point spread functions $h_1(x, y)$ through $h_3(x, y)$ corresponding to each of the depth positions D1 through D3 stored in an LUT (Look Up Table). The image processing means 60 selects a point spread function to be employed in a blood vessel emphasizing process to be administered onto each fluorescent image FP according to the judgment results of the depth position judging means 50.

The image processing means 60 administers a blood vessel emphasizing process onto the fluorescent images FP employing the selected point spread functions. Here, if the pixel values of an actually obtained fluorescent image FP are designated to be $g(x, y)$, it may be considered that the fluorescent image $g(x, y)$ is observed by convoluting a point spread function $h(x, y)$ with a true fluorescent image $f(x, y)$, if noise is ignored. Accordingly, the image processing means 60 performs calculations to deconvolute the point spread function $h(x, y)$ from the fluorescent image $g(x, y)$, to obtain the true fluorescent image $f(x, y)$. Note that a known method, such as inverse Fourier transform, in which the fluorescent image $g(x, y)$ undergoes Fourier transform, then divided by a function $H(x, y)$, which is the point spread function $h(x, y)$ after undergoing Fourier transform, may be employed as the deconvoluting calculation.

Here, because the degree of fluorescent scattering within living tissue differs among the depth positions D1 through D3 of the blood vessels, the point spread function $h(x, y)$ differs for each of the depth positions D1 through D3. In other words, the degree of blur of blood vessels within fluorescent images FP differs according to the depth positions of the blood vessels pictured therein. Therefore, the image processing means 60 has stored therein the plurality of point spread functions $h(x, y)$, corresponding to each of the depth positions D1 through D3, which are obtained by observation in advance. The aforementioned deconvoluting calculation is performed after selecting a point spread function from among the point spread functions $h_1(x, y)$ through $h_3(x, y)$ according to the depth position D1, D2, or D3 of the blood vessels judged by the depth position judging means 50.

A display control means 70 illustrated in FIG. 1 displays the standard observation images P0, the fluorescent images FP, and the estimated spectral images generated by the spectral image obtaining means 40 on a display device 3, such as a liquid crystal display and a CRT. Note that the display control means 70 functions to administer processes, such as inverse gamma conversion, a mirror image process, and display of information regarding each of the aforementioned images as text data simultaneously along with the images.

In this manner, the depth position D1, D2, or D3 of the blood vessels is detected from the spectral images SP1 and SP2, by utilizing the fact that penetration depths of light into living tissue differ according to the wavelength of light. Then, images of fluorescence emitting blood vessels are corrected according to the detected depth position D1, D2, or D3. Thereby, even if the degree of blur of the blood vessel image differs within the fluorescent images FP due to the depth position D thereof, correction can be performed using image processing conditions RC which are optimal for each depth position D. Accordingly, the image quality of the fluorescent images FP can be improved, and diagnostic efficiency can be improved.

Figure 4:
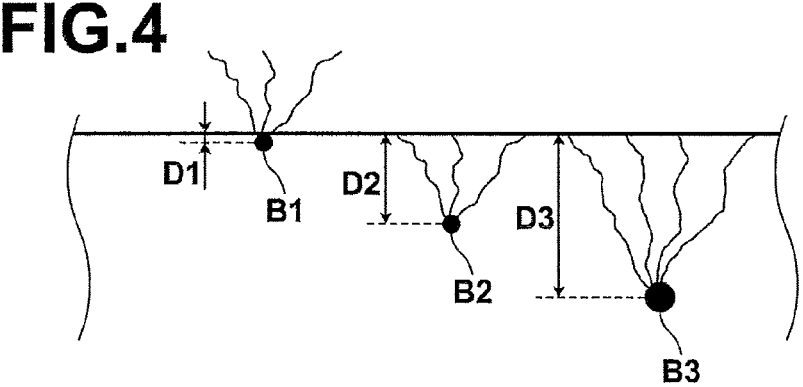
FIG. 4 is a schematic diagram that illustrates the relationship between depths within living tissue and the degree of fluorescent scattering.
Figure 5A:
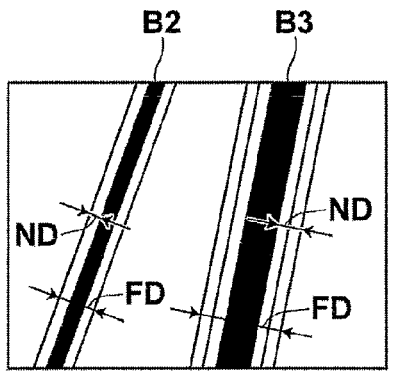
FIG. 5A and FIG. 5B illustrate an example of a fluorescent image in which blood vessels are blurred, and an example of a corrected fluorescent image, respectively.
Figure 5B:
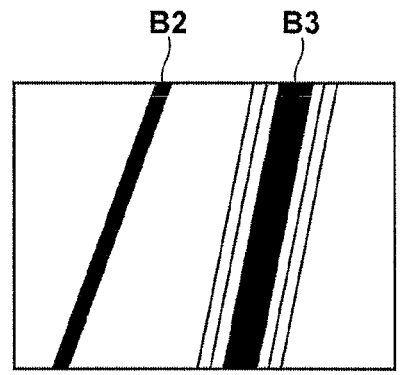

That is, the degree that fluorescence emitted from blood vessels scatters differs at the depth positions D1, D2, and D3 of blood vessels which are dyed by fluorescent pigment, as illustrated in FIG. 4. Accordingly, the degree of blur of blood vessel images within fluorescent images FP differ at a depth position D2 and a depth position D3, as illustrated in FIG. 5A, for example. In the case that a blood vessel B2 at depth position D2 and a blood vessel B3 at depth position D3 are corrected using the same image processing conditions RC, the image quality of the blood vessel B3 may not be improved, as illustrated in FIG. 5B.

On the other hand, the present invention changes the image processing conditions RC according to the depth position D of blood vessels as judged by the depth position judging means 50. Therefore correction can be performed using image processing conditions RC which are optimal for each depth position D. Accordingly, the image quality of the fluorescent images FP can be improved, and diagnostic efficiency can be improved.

Note that a case has been described in which the image processing means 60 employs the point spread functions $h(X, y)$ to perform the blood vessel emphasizing process. Alternatively, blood vessel images may be extracted, and the extracted blood vessel images may be overlapped onto the fluorescent images, to perform the blood vessel emphasizing process. Specifically, the image processing means 60 may extract the outlines of blood vessels, based on the widths of fluorescence FD and blur spread ND (refer to FIG. 5A) within a fluorescent image FP, and performs the blood vessel emphasizing process by overlapping the extracted outlines of the blood vessels onto the fluorescent image FP. That is, because the width of blur spread differs at the depth positions D2, D2, and D3 of blood vessels, the widths of blur spread ND that differ at each depth position are stored as image processing conditions RC. Then, the image processing means 60 selects a blur spread width ND to be employed to extract the outlines of blood vessels according to the depth positions D1, D2, or D3 thereof, and extracts the outline of the blood vessels by subtracting the blur spread width ND from the fluorescence width FD. In this case as well, correction can be performed using image processing conditions RC which are optimal for each depth position D. Accordingly, the image quality of the fluorescent images FP can be improved, and diagnostic efficiency can be improved.

FIG. 6 is a flow chart that illustrates a preferred embodiment of the image processing method of the present invention. The image processing method of the present invention will be described with combined reference to FIG. 1 through FIG. 6. First, living tissue within a body cavity is imaged by the endoscope 1 in a state in which blood vessels are dyed with fluorescent pigment. At this time, a standard observation image P0, which is obtained while the tissue is being irradiated with white light, and a fluorescent image FP, which is obtained while the tissue is being irradiated with an excitation light beam, are obtained of the same portion within the body cavity (Step ST1). Thereafter, preliminary processes are administered by the preliminary processing means 32, and a region of interest ROI is set (Step ST2).

Next, the spectral image obtaining means 40 generates a plurality of spectral images SP1 and SP2 having different wavelength ranges, based on the standard observation image P0 (Step ST3). Then, the depth position judging means 50 judges the depth position D of a blood vessel which is pictured within the region of interest ROI, based on the plurality of spectral images SP1 and SP2 (Step ST4). Thereafter, the image processing means 60 administers an image process using image processing conditions RC corresponding to the depth position D of the blood vessel (Step ST5), and the processed image is displayed by the display device 3 (Step ST6).

According to the embodiments described above, the plurality of spectral images SP1 and SP2 that include a blood vessel dyed with fluorescent pigment, each of which being of a different wavelength range, and the fluorescent image FP, which is imaged while the excitation light beam is irradiated onto the blood vessels, are obtained. The depth position D at which the blood vessel exists is judged, employing the plurality of obtained spectral images SP1 and SP2. The image processing conditions RC are changed according to the depth position D of the blood vessel, judged by the depth position judging means 50, and the blood vessel emphasizing process is administered on the fluorescent image FP. That is, the depth position D of the blood vessel is ascertained from the spectral images SP1 and SP2, by utilizing the fact that penetration depths of light into living tissue differ according to the wavelength of light. Then, image processing conditions RC suited to the depth position D of the blood vessel are employed to administer the blood vessel emphasizing process onto the fluorescent image FP, in which blood vessel images appear differently according to the depth positions D thereof. Therefore, the sharpness and resolution of the blood vessel image can be improved.

A configuration is adopted, in which the image processing conditions RC which are changed by the image processing means 60 are a plurality of point spread functions h1(x, y) through h3(x, y) corresponding to the depth positions D of the blood vessels; and the image processing means 60 selects a point spread function h(x, y) to be employed to process the fluorescent image FP corresponding to the judgment results obtained by the depth position judging means 50. Therefore, even if the degree of blur of the blood vessel image differs within the fluorescent image due to scattering of fluorescence or the like, image processing conditions RC suited for the depth position D of the blood vessels can be employed to administer the blood vessel emphasizing process. Therefore, the sharpness and resolution of the blood vessel images can be improved.

Alternatively, the image processing means 60 may extract the outlines of the blood vessels, based on the widths of fluorescence FD and blur spread ND within the fluorescent image, and may administer the blood vessel emphasizing process by overlapping the extracted outlines of the blood vessels onto the fluorescent image FP, as illustrated in FIG. 5A. The widths of blur spread ND, which differ according to the depth position D of the blood vessels, may be the image processing conditions RC. In this case, even if the degree of blur of a blood vessel image differs within the fluorescent FP image due to scattering of fluorescence or the like, the width of blur spread ND can be set according to the depth position D of the blood vessel. Therefore, the sharpness and resolution of the blood vessel image can be improved.

The plurality of spectral images SP1 and SP2 are estimated spectral images, which are generated by administering matrix calculations onto the standard observation image P0 obtained by imaging the subject irradiated with white light. Therefore, spectral images of different wavelengths, each having different penetration depths, can be obtained efficiently.

Further, the depth position judging means 50 judges the depth position D of the blood vessels based on the penetration depth of the wavelengths of the spectral images SP1 and SP2, by judging whether blood vessel images can be extracted from each of the spectral images SP1 and SP2. Therefore, the depth position D of blood vessels can be accurately judged from the spectral images SP1 and SP2, by utilizing the fact that penetration depths of light into living tissue differ according to the wavelength of light.

As illustrated in FIG. 3, the spectral images include the first spectral image SP1 obtained by light having a wavelength of approximately 430 nm, and the second spectral image SP2 obtained by light having a wavelength of approximately 570 nm. The depth position judging means 50 comprises: the blood vessel image extracting means 51 for extracting the blood vessel images from each of the first spectral image SP1 and the second spectral image SP2; the blood vessel presence judging means 52 for judging whether the blood vessel images are present in each of the spectral images SP1 and SP2, based on the extraction results obtained by the blood vessel image extracting means 51; and depth position detecting means 53, for judging that the blood vessels are at a first depth position D1 close to the surface in the case that the blood vessel presence judging means 52 judges that the blood vessel images are present within the first spectral image SP1, judging that the blood vessels are at a second depth position D2 deeper than the first depth position D1 in the case that the blood vessel presence judging means 52 judges that the blood vessel images are present within the second spectral image SP2, and judging that the blood vessels are at a third depth position D3 deeper than the second depth position D2 in the case that the blood vessel presence judging means 52 judges that the blood vessel images are present in neither the first spectral image SP1 nor the second spectral image SP2. Therefore, the depth position D of the blood vessels can be judged accurately.

The image processing apparatus further comprises: the region of interest setting means 33 for setting a region of interest ROI within the fluorescent image. The judgment of the depth position D of the blood vessels by the depth position judging means 50 and the image process administered by the image processing means 60 are performed within the region of interest ROI set by the region of interest setting means 33. Therefore, the time required for image processing may be shortened, and processing can be performed efficiently.

The present invention is not limited to the embodiments described above. For example, the depth position judging means 50 illustrated in FIG. 3 detects the depth position D1, D2, or D3 of the blood vessel from two spectral images SP1 and SP2. Alternatively, the depth position D of blood vessels may be detected from more than two spectral images SP. In this case, a spectral image SP is obtained for each of a plurality of different wavelengths having different penetration depths. For example, in the embodiments described above, the depths of blood vessels are divided into three depth positions D1 through D3. However, in the case that the depth position D is divided into five depth positions, the spectral image obtaining means 40 generates four or more spectral images, and the depth position judging means 50 employs the four or more spectral images to judge the depth position D of blood vessels. As a further alternative, the depth position judging means 50 may judge the depth position D from a spectral image having a wavelength of 750 nm, using the absorption of fluorescent pigment as a reference.

In addition, a case has been described in which the spectral images SP1 and SP2 for detecting the depth position D of the blood vessels are estimated spectral images generated by matrix calculations employing the standard observation image P0. Alternatively, the depth position D may be detected using spectral images SP1 and SP2 which are obtained employing optical filters. In this case, the spectral images SP1 and SP2 are those which are obtained by imaging the blood vessels while they are being irradiated by light of two wavelengths (390 nm to 445 nm, and 530 nm to 550 nm), which are employed in narrow band imaging.

Further, in the embodiments described above, a single point spread function h(x, y) is selected for a single region of interest ROI within the fluorescent image FP to perform the blood vessel emphasizing process. Alternatively, a different point spread function h(x, y) corresponding to the depth positions D of each blood vessel may be employed to perform the blood vessel emphasizing process for the blood vessel images. For example, there are cases in- which blood vessels which are pictured within a fluorescent image FP are at different depth positions, as illustrated in FIGS. 5A and 5B. In these cases, the depth position judging means 50 may divide the fluorescent image FP (or the region of interest ROI) into a plurality of regions and judge the depth position D of a blood vessel in each of the plurality of regions based on the spectral images SP1 and SP2. Thereafter, the image processing means 60 may administer blood vessel emphasizing processes employing point spread functions h(x, y) corresponding to the depth positions D of each blood vessel in each region. If this configuration is applied to the example illustrated in FIG. 5B, a blood vessel emphasizing process employing point spread function h2(x, y) is administered on the blood vessel image B2 at depth position D2, and a blood vessel emphasizing process employing point spread function h3(x, y) is administered on the blood vessel image B3 at depth position D3.

In the embodiments described above, judgment of the depth position D of blood vessels is performed with respect to the region of interest ROI. Alternatively, judgment of the depth position D of blood vessels may be performed with respect to the entire region of the standard observation image P0 and the fluorescent image FP.

A case has been described in which the image processing apparatus 30 of the endoscope 1 is constituted by a DSP or the like. Alternatively, the image processing apparatus 30 may be realized by executing an image processing program, which is read into an auxiliary memory device, on a computer (a personal computer, for example). The image processing program may be distributed being recorded on to a recording medium such as a CD-ROM, or distributed via a network such as the Internet, then installed into the computer.

What is claimed is:

1. An image processing apparatus, comprising:
a processor programmed to execute a method including:
obtaining a standard observation image obtained by imaging blood vessels irradiated with white light and a fluorescent image by imaging fluorescence emitted by substances within the blood vessels when an excitation light beam is irradiated onto the blood vessels;
generating a plurality of spectral images, each of a different wavelength range, of the same blood vessels of which the fluorescent image is obtained, by administering matrix calculations onto the standard observation image according to matrix parameters that are extracted from a database as corresponding to respective wavelengths of the spectral images to be generated;
judging whether blood vessel images are present in each of the plurality of spectral images and judging the depth position at which the blood vessels exist based on a wavelength corresponding to the spectral image in which the blood vessel images are judged to be present; and
changing image processing conditions according to the judged depth position of the blood vessels, and administering a blood vessel emphasizing process on the fluorescent image.

2. An image processing apparatus as defined in claim 1, wherein:
the image processing conditions which are changed are a plurality of point spread functions corresponding to the depth positions of the blood vessels; and
the processor is further programmed to select a point spread function to be employed to process the fluorescent image corresponding to the judgment results obtained by the depth position judging, and administer the blood vessel emphasizing process on the fluorescent image.

3. An image processing apparatus as defined in claim 1, wherein:
the outlines of the blood vessels are extracted, based on the widths of fluorescence and blur spread within the fluorescent image, and the blood vessel emphasizing process is administered by overlapping the extracted outlines of the blood vessels onto the fluorescent image; and
the widths of blur spread, which differ according to the depth position of the blood vessels, are the image processing conditions.

4. An image processing apparatus as defined in claim 1, wherein:

the plurality of spectral images are estimated spectral images, which are generated by administering matrix calculations onto a standard observation image obtained by imaging the blood vessels irradiated with white light.

5. An image processing apparatus as defined in claim 1, wherein:
the plurality of spectral images are obtained by irradiating two narrow bandwidth light beams having different wavelength ranges onto the blood vessels, and imaging the blood vessels to obtain spectral images corresponding to each narrow wavelength band.

6. An image processing apparatus as defined in claim 1, wherein:
the depth position of the blood vessels is judged based on the penetration depth of the wavelengths of the spectral images, by judging whether blood vessel images can be extracted from each of the spectral images.

7. An image processing apparatus as defined in claim 6, wherein:
the spectral images include a first spectral image obtained by light having a wavelength of approximately 430 nm, and a second spectral image obtained by light having a wavelength of approximately 570 nm; and
the method which the processor is programmed to execute further includes:
extracting the blood vessel images from each of the first spectral image and the second spectral image;
judging whether the blood vessel images are present in each of the spectral images, based on the extraction results obtained by the blood vessel image extracting; and
judging that the blood vessels are at a first depth position close to the surface in the case that the blood vessel presence judging judges that the blood vessel images are present within the first spectral image, judging that the blood vessels are at a second depth position deeper than the first depth position in the case that the blood vessel presence judging judges that the blood vessel images are present within the second spectral image, and judging that the blood vessels are at a third depth position deeper than the second depth position in the case that the blood vessel presence judging judges that the blood vessel images are present in neither the first spectral image nor the second spectral image.

8. An image processing apparatus as defined in claim 1, wherein the method which the processor is programmed to execute further includes:
setting a region of interest within the fluorescent image; and wherein:
the judgment of the depth position of the blood vessels by the depth position judging and the administered blood vessel emphasizing process are performed within the region of interest set by the region of interest setting.

9. An image processing method carried out by an image processing apparatus, comprising:
executing by a processor a method including:
obtaining a standard observation image obtained by an imaging element by imaging blood vessels irradiated with white light and a fluorescent image obtained by an imaging element by imaging fluorescence emitted by substances within the blood vessels when an excitation light beam is irradiated onto the blood vessels;
generating a plurality of spectral images, each of a different wavelength range, of the same blood vessels of which the fluorescent image is obtained, by administering matrix calculations onto the standard observation image according to matrix parameters that are extracted from a database as corresponding to respective wavelengths of the spectral images to be generated, carried out by the image processing apparatus;
judging whether blood vessel images are present in each of the plurality of spectral images and judging the depth position at which the blood vessels exist based on a wavelength corresponding to the spectral image in which the blood vessel images are judged to be present, carried out by the image processing apparatus;
changing image processing conditions according to the depth position of the blood vessels, carried out by the image processing apparatus; and
administering a blood vessel emphasizing process on the fluorescent image, carried out by the image processing apparatus.

10. A non-transitory computer readable medium in which an image processing program is recorded, the program causing a computer to execute the procedures of:
obtaining a standard observation image obtained by imaging blood vessels irradiated with white light and a fluorescent image by imaging fluorescence emitted by substances within the blood vessels when an excitation light beam is irradiated onto the blood vessels;
generating a plurality of spectral images, each of a different wavelength range, of the same blood vessels of which the fluorescent image is obtained, by administering matrix calculations onto the standard observation image according to matrix parameters that are extracted from a database as corresponding to respective wavelengths of the spectral images to be generated;
judging whether blood vessel images are present in each of the plurality of spectral images and judging the depth position at which the blood vessels exist based on a wavelength corresponding to the spectral image in which the blood vessel images are judged to be present;
changing image processing conditions according to the judged depth position of the blood vessels; and
administering image processes on the fluorescent image.

* * * * *